United States Patent [19]

Paulis

[11] Patent Number: 4,738,678
[45] Date of Patent: Apr. 19, 1988

[54] DIAPER/WIPE COMBINATION

[76] Inventor: Robert A. Paulis, 487 Carolina St., Anacortes, Wash. 98221

[21] Appl. No.: 24,611

[22] Filed: Mar. 11, 1987

[51] Int. Cl.[4] ............................................. A61F 13/16
[52] U.S. Cl. ................................................. 604/385 R
[58] Field of Search .................. 604/385.1, 385.2, 358, 604/386, 387

[56] References Cited

U.S. PATENT DOCUMENTS 4,221,221 9/1980 Ehrlich ......................... 604/385.1 X
4,417,894 11/1983 Norris ............................ 604/385.1

Primary Examiner—John D. Yasko
Attorney, Agent, or Firm—Graybeal, Jensen & Puntigam

[57] ABSTRACT

A disposable diaper package including means (6, 8, 10, 12) for simultaneously retaining the diaper (2) in its collapsed, folded sanitary condition and retaining a premoistened wipe/towelette (4) such that when the diaper (2) is released and unfolded, the towelette (4) becomes immediately available.

3 Claims, 2 Drawing Sheets

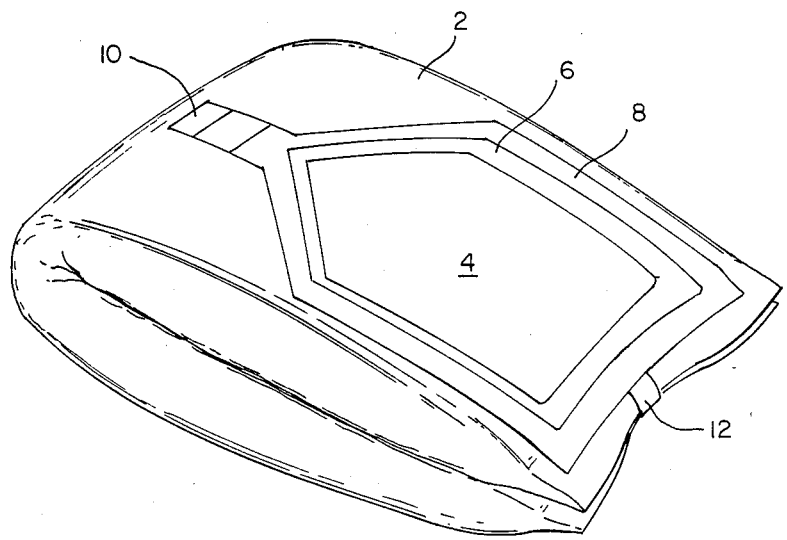
FIG. 1
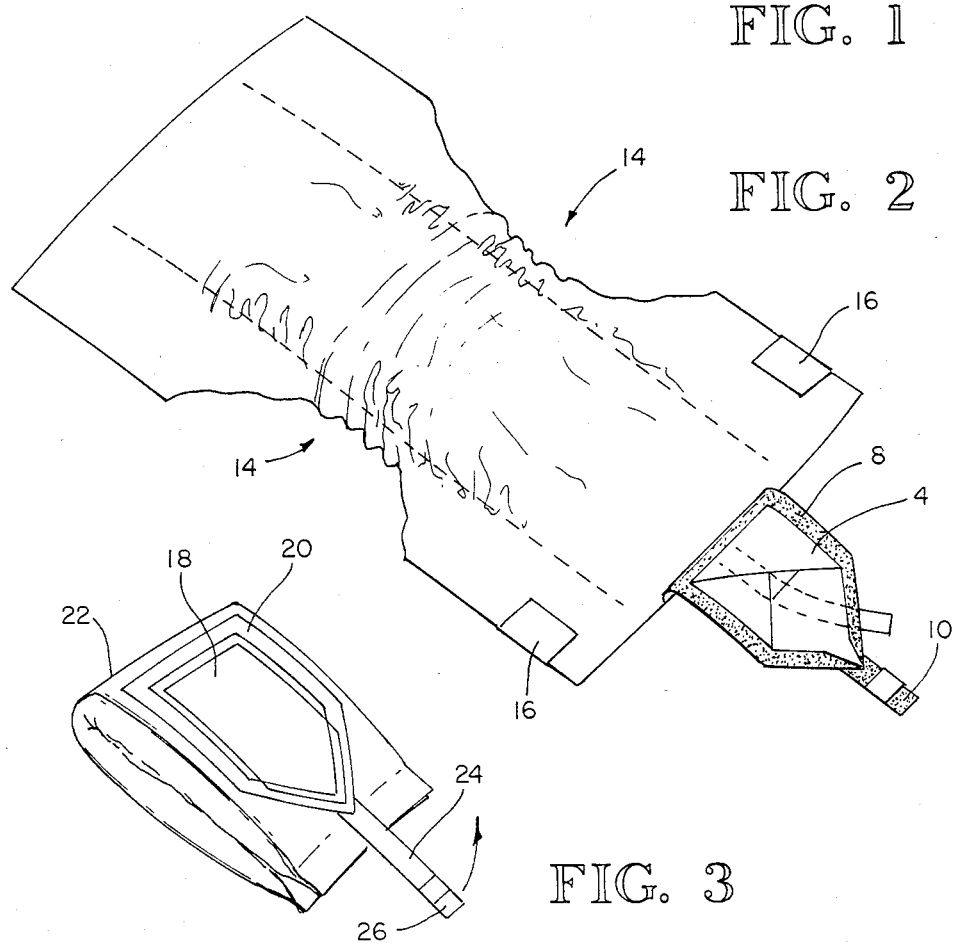
FIG. 2
FIG. 3

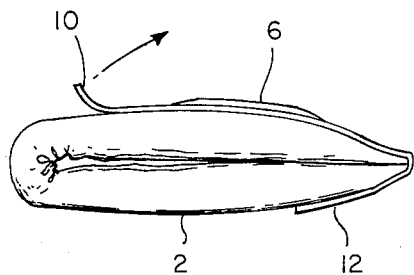
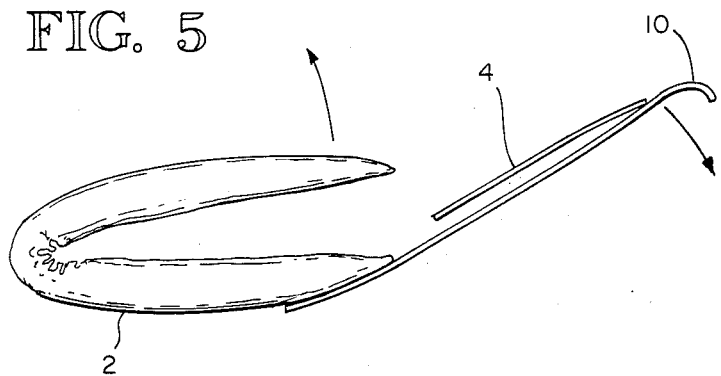

DIAPER/WIPE COMBINATION

TECHNICAL FIELD

This invention relates to disposable diapers and in particular to a device which retains the diaper in a compact, folded form when removed from the box while at the same time making available to the user a moistened wipe for cleaning the diaper user.

BACKGROUND ART

Disposable diapers are well known and it is also well known that it is often necessary to have a method for cleaning the diaper user prior to the application of a new diaper.

It is also well known to prepackage two elements which are designed to be used together.

The particular invention, however, deals with a combination of a dispoable diaper and a moisturized wipe pad or sheet for cleaning the user. The inventive combination utilizes the means for attaching the wipe to also secure the diaper in a compact folded form even when removed from the box. Traditionally, disposable diapers come prepackaged in a box or other container in a somewhat compressed form. When the diapers are removed from the box to be placed in a diaper bag or the like, they need to be secured with a rubberband or other method to prevent them from unfolding, expanding and taking up a great deal of room. The diaper is now more likely to become contaminated.

Prior art known to the inventor, dealing with both disposable diapers and combination packages include U.S. Pat. No. 2,637,439 granted to Banks on May 5, 1953 which teaches the combination of a single use towel having a soap cartridge folded therein.

U.S. Pat. No. 2,916,037 granted to Hansen Dec. 8, 1959 teaches the broad concept of a multi-layer disposable diaper.

U.S. Pat. No. 3,561,456 granted to Stuart, Jr. Feb. 9, 1971 teaches the concept of a combination of a moist washing solution encapsulated in a drying member.

U.S. Pat. No. 3,585,999 granted to Wamberg June 22, 1971 teaches the concept of a disposable diaper having front covering which is attached only along the top edge which may be used to clean the user and also used to cover the soiled area of the diaper.

U.S. Pat. No. 3,635,567 granted to Richardson, Jr. on Jan. 18, 1972 teaches the combination of a disposable applicator unit including a selectively releasable liquid and an absorbent pad material for applying the liquid.

U.S. Pat. No. 3,794,038 granted to Buell Feb. 26, 1974 discloses a disposable diaper wherein the top sheet of the diaper i.e. the plastic portion may be easily detached from the diaper and separately disposed.

U.S. Pat. No. 3,926,189 granted to Taylor Dec. 16, 1975 discloses a disposable diaper having an auxiliary pad which is selectively positionable within the diaper for appropriate absorbency.

U. S. Pat. No. 4,417,894 granted Nov. 29, 1983 to Norris discloses a disposable diaper having a towel sheet superposed on the back sheet of the diaper which may be unfastened and used as a towel to clean the child.

With the above noted prior art in mind, it is an object of the present invention to provide a disposable diaper which remains in compact sanitary form when removed from the bulk package.

It is another object of the present invention to provide a disposable diaper which when opened and ready for use places a premoistened towelette for cleaning at the disposal of the user.

It is yet another object of the present invention to provide a disposable diaper wherein the securement and packaging for a premoistened towelette likewise secures the diaper in a compact folded sanitary configuration.

Still a further object of the present invention is to provide a disposable diaper which is secured in a compact folded sanitary configuration such that when the securement is released so that the diaper can be open for use a premoistened towelette is automatically dispensed.

Another object of the present invention is to provide a moistened towelette with each diaper to encourage the use thereof resulting in greater sanitation.

BRIEF DESCRIPTION OF THE DRAWINGS

FIG. 1 is a representation of the preferred embodiment of the present invention in its closed sanitary condition.

FIG. 2 is a representation of the preferred embodiment of the present invention in an open conditions showing the moistened wipe.

FIG. 3 is an illustration of an alternate embodiment of the present invention in a partially opened condition.

FIG. 4 is a side elevation view of the embodiment of FIG. 1 in a folded, sanitary condition illustrating the opening process.

FIG. 5 is a side elevation of the embodiment of FIG. 1 in a partially opened condition.

DETAILED DESCRIPTION OF THE DRAWINGS

As seen in FIG. 1, the disposable diaper 2 is shown in its folded sanitary condition. Secured to the outer surface of the diaper is a premoistened wipe 4 which is located within a water impermeable pocket 6 which is then sealed about the entire periphery as at 8. The end of the water impermeable pocket adjacent the fold of the diaper includes a non-adhesively secured tab 10 such that it may be grasped and pulled outwardly releasing the towelette. The end of the pocket 6 which is adjacent the cut end of the diaper 2 includes an adhesive tab 12 which wraps around the end and secures the diaper in a folded compact condition.

As the user pulls the tab and releases the diaper, the towelette or wipe is also released and is readily at hand for the user.

Referring now to FIG. 2, it can be seen that the diaper is, as is known, cut, pleated or otherwise reduced at 14 to accommodate the legs of the user, and includes adhesive tabs 16 for securing the diaper at the waist when placed upon the child. This view further shows the premoistened towelette 4 including extension 5 which would normally be grasped when utilizing the pull tab 10, now released from the envelope 6 and ready for use. The adhesive section 8 is readily visible as is the tab 10. When in use, the entire enclosure 8, 10, 12 would be removed.

Referring now to FIG. 3, the alternate embodiment has a premoistened towelette 18 in an envelope 20 secured to the exterior portion of a disposable diaper 22 having a single tab extending from the end of the towelette adjacent the open or cut end of the diaper. When packaged this tab 24 will be secured around the end and thus hold the diaper in a compact position. The outer end 26 of tab 24 is non-adhesive for easy grasping to release the diaper and the towelette.

Referring now to FIG. 4, it becomes apparent that the combination of the envelope 6 and the adhesive 8 and strip 12 hold the diaper in its compact folded sanitary condition.

FIG. 5 depicts the process of opening of the diaper by pulling upon tab 10 releasing the towelette 4 and allowing the upper half of the diaper 2 to move to its unfolded condition for ready use. As seen in this view, the towelette extension 5 would retain the towelette in a convenient location.

It is contemplated that the diaper may include, since it is maintained in a folded sanitary condition, powder.

Thus as can be seen, the present invention discloses an extremely convenient inexpensive method of providing the user of diapers with a readily available cleaning device while at the same time maintaining the folded diaper in a sanitary, compact configuration.

I claim:

1. A disposable diaper/wipe combination including an integral premoistened cleaning device comprising:

a preformed diaper folded inwardly upon itself such that the majority of the portion designed to contact the skin of the baby is shielded by the exterior air and water impermeable sheet, means for retaining the diaper in its folded, sanitary condition, and for retaining the premoistened cleaning device in position comprising an elongated air and water impermeable band including a widened portion intermediate its ends sealingly secured to the exterior of the diaper, extending from one side, around the unfolded edge to be secured to the opposite side, a premoistened cleaning device sealingly held in place beneath the widened portion for instant release when the band is removed to open the diaper whereby the user has immediate access to the cleaning device at the time of need.

2. A diaper/wipe combination as in claim 1, wherein the means for retaining the diaper in its folded condition includes a tab for easy opening and removal prior to use.

3. A diaper/wipe combination as in claim 2, wherein the wipe includes an extension adjacent the tab facilitating grasping the extension and the tab simultaneously.

* * * * *